United States Patent [19]

Wolf

[11] Patent Number: 5,507,819
[45] Date of Patent: Apr. 16, 1996

[54] APPARATUS AND METHOD FOR STABILIZING A HUMERAL HEAD IN A SHOULDER

[76] Inventor: Eugene M. Wolf, 55 Montecito Rd., San Rafael, Calif. 94901

[21] Appl. No.: 333,478

[22] Filed: Nov. 2, 1994

[51] Int. Cl.⁶ .................. A61F 2/40; A61F 2/30
[52] U.S. Cl. .................. 623/19; 623/22; 623/18
[58] Field of Search .................. 623/16, 18, 22, 623/23, 19

[56] References Cited

U.S. PATENT DOCUMENTS

| | | | |
|---|---|---|---|
| 3,803,641 | 4/1974 | Golyakhovsky | 128/92 |
| 3,842,442 | 10/1974 | Kolbel | 128/92 |
| 3,979,778 | 9/1976 | Stroot | 128/92 |
| 4,045,826 | 9/1977 | Stroot | 128/92 |
| 4,550,450 | 11/1985 | Kinnett | 623/18 |
| 4,693,723 | 9/1987 | Gabard | 623/19 |
| 4,919,669 | 4/1990 | Lannelongue | 623/19 |
| 4,955,919 | 9/1990 | Pappas et al. | 623/22 |
| 4,964,865 | 10/1990 | Burkhead et al. | 623/19 |
| 4,986,833 | 1/1991 | Worland | 623/19 |
| 5,030,219 | 7/1991 | Matsen, II et al. | 606/53 |
| 5,032,132 | 7/1991 | Matsen, III et al. | 623/19 |

FOREIGN PATENT DOCUMENTS

| | | |
|---|---|---|
| 2541890A1 | 9/1984 | France . |
| 2541890 | 9/1984 | France ................ 623/22 |
| 2578162 | 9/1986 | France ................ 623/22 |
| 2634372 | 1/1990 | France ................ 623/22 |
| 2660546 | 10/1991 | France ................ 623/22 |
| 2676172 | 11/1992 | France ................ 623/22 |
| 2166654A | 5/1986 | United Kingdom . |

*Primary Examiner*—David Isabella
*Attorney, Agent, or Firm*—Limbach & Limbach

[57] ABSTRACT

A prosthetic glenoid for use in the shoulder is comprised of a cup having three flanges. To prepare the shoulder for implantation of the cup, the glenoid fossa is reamed to a depth at which the acromion, coracoid, and lateral portion of the scapula form a tri-flanged configuration. The cup is proportioned to be positioned in the reamed glenoid fossa such that each of the three flanges of the cup corresponds to one of the three bones forming the tri-flanged configuration of bone.

4 Claims, 3 Drawing Sheets

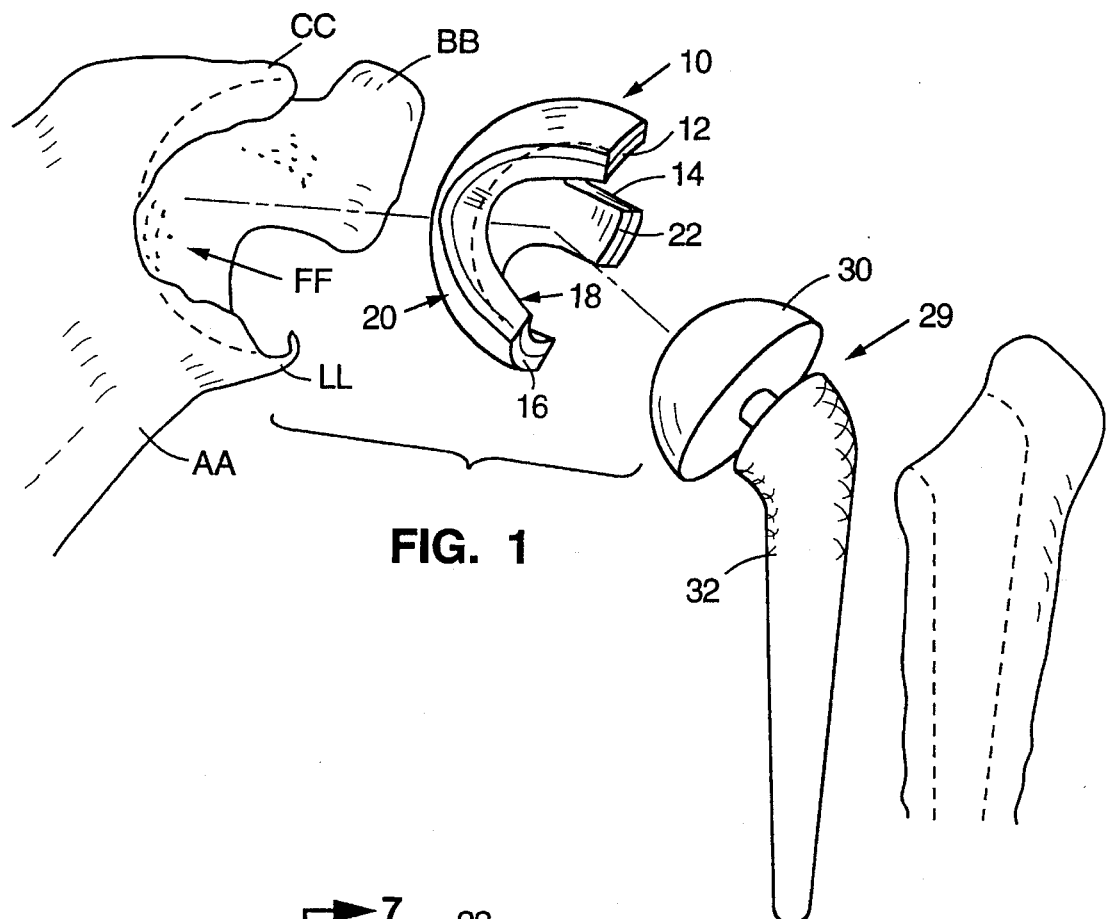
FIG. 1
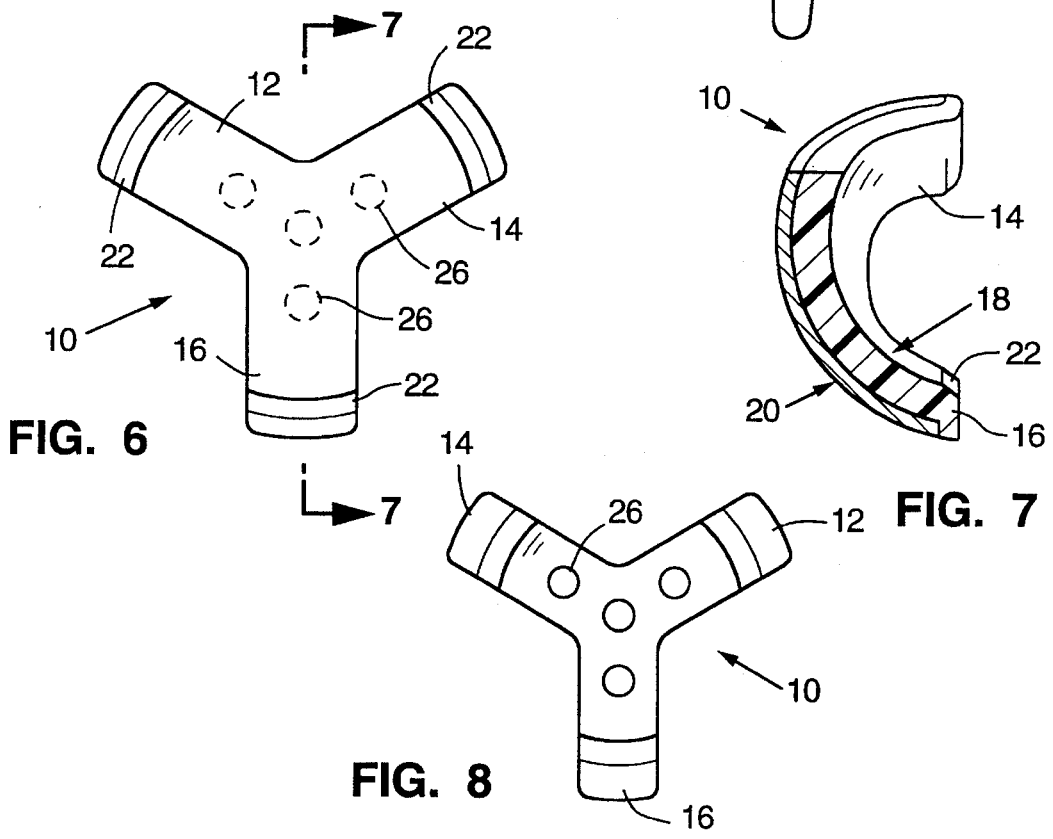
FIG. 6
FIG. 7
FIG. 8

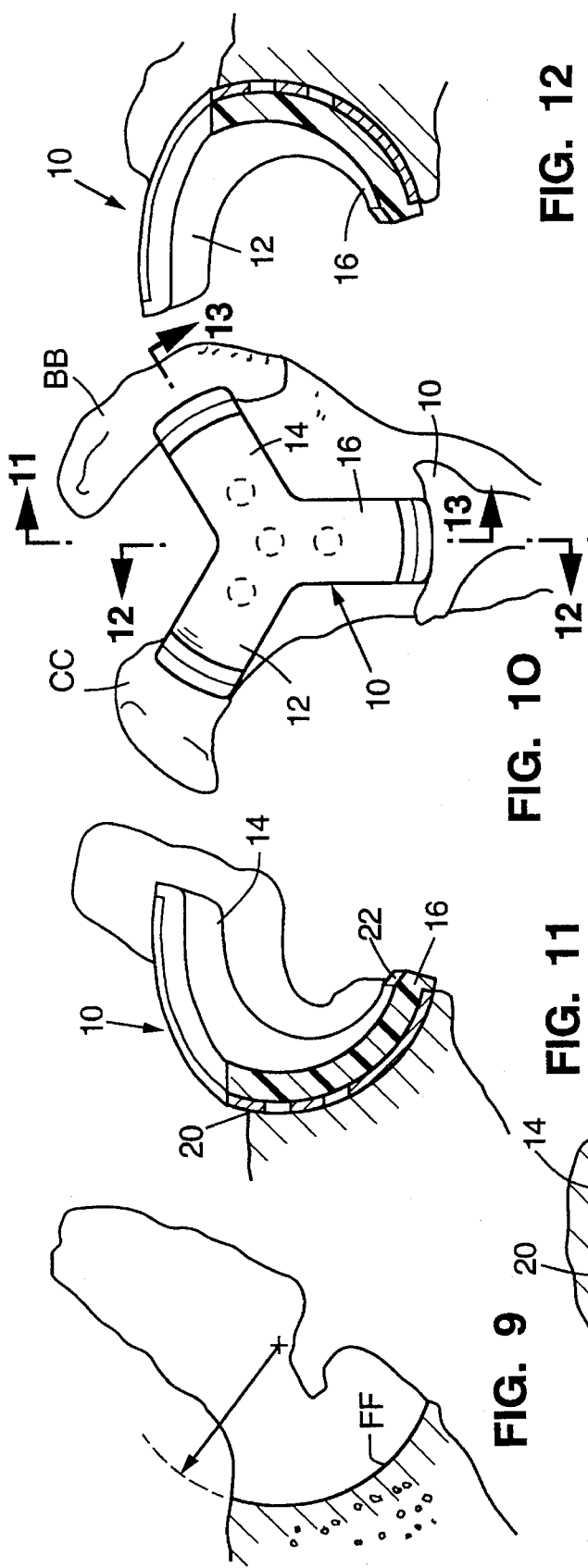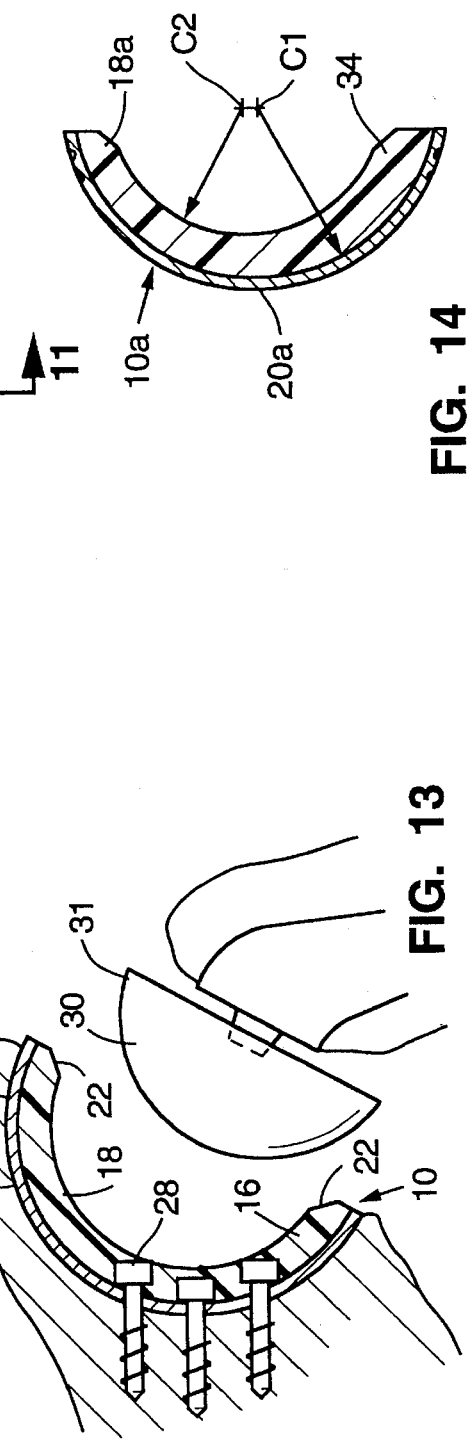

APPARATUS AND METHOD FOR STABILIZING A HUMERAL HEAD IN A SHOULDER

FIELD OF INVENTION

The present invention relates to the field of shoulder prostheses and particularly to a tri-flanged glenoid component and a method for implanting it.

BACKGROUND OF INVENTION

At the gleno-humeral joint in the shoulder, the head of the humerus (which is the bone of the upper arm), articulates against the glenoid fossa for upper arm movement. The articulating surfaces are normally separated by cartilage which reduces friction between the articulating surfaces. The head (designated GG in FIG. 5) is held into place and its stability maintained by ligaments and muscle tissue (collectively designated HH in FIG. 5) surrounding the joint.

Damage to, or deterioration of these bones or the cartilage separating them often necessitates implantation of prosthetic glenoid and humeral components. Many candidates for shoulder prostheses suffer from rotator cuff arthropathy, a condition caused by disease, injury, or aging in which the muscle tissue of the shoulder is damaged or degenerated. Because stability of the shoulder joint depends solely on the integrity of the surrounding muscle tissue, these patients lack the tissue which is essential for holding the shoulder joint together.

The designs of some existing shoulder prostheses are directed towards solving the problem of unstable shoulder joints. Many involve mechanically linking the humeral component to the glenoid component, a procedure which severely limits the range of motion of the shoulder.

Ball and socket devices similar to hip prostheses are sometimes used in the shoulder. In typical ball and socket devices, a humeral component is provided which has a stem fixed inside the intermedullary canal of the humerus, and a spherical ball connected to its distal end. The spherical ball serves as a substitute for the patient's humeral head, which is removed prior to implantation of the humeral component. A cup attached to the glenoid fossa provides a surface upon which the ball articulates during arm movement.

The ball and socket type of shoulder implants are used for patients who, because of arthritis, have suffered from serious deterioration of the cartilage. Because the cartilage in a healthy shoulder provides a smooth surface against which the humeral head articulates, the humeral head of a patient having deteriorated cartilage articulates directly against the glenoid and thus suffers from serious pain. The ball and socket implants eliminate the pain by providing smooth articulating surfaces in the shoulder. However, these implants are not suitable for patients having rotator cuff arthropathy, because they provide no structure to keep the humeral head from migrating away from the articulating surface of the socket. Candidates for conventional ball and socket joints are patients who do not have damaged rotator cuffs and who therefore retain the tissue needed to prevent migration of the humeral head.

OBJECT AND SUMMARY OF THE INVENTION

The object of the present invention is to provide a prosthetic glenoid component which stabilizes the shoulder joint but which does not restrict range of motion of the shoulder.

The present invention is a prosthetic glenoid component for implantation in the shoulder. To prepare for implantation of the prosthetic component, the glenoid in the patient's shoulder is reamed spherically to form a bony cup. Reaming is performed to a depth which exposes the tri-flanged configuration of the acromion, scapula, and coracoid process. The prosthetic glenoid component is likewise tri-flanged and is proportioned such that when it is positioned within the reamed bony cup at the glenoid, the flanges of the prosthesis approximately correspond to the flanges of the reamed glenoid.

DESCRIPTION OF THE DRAWINGS

FIG. 1 is a perspective view of the glenoid prosthesis of the present invention.

FIG. 6 is a forward view of a glenoid component of the apparatus of the present invention.

FIG. 7 is a cross-sectional side view of the glenoid component of FIG. 6 taken along the plane designated 6—6 in that figure.

FIG. 8 is a rear view of a glenoid component of the apparatus of the present invention.

FIG. 9 is an anterior view of the bones of a shoulder joint showing, in cross-section, the glenoid fossa after it has been reamed according to the present invention.

FIG. 10 is a lateral view of a scapula showing placement of the glenoid prosthesis of the present invention.

FIG. 11 is a cross-section view taken along the plane designated 11—11 in FIG. 10 showing the bones of a shoulder joint and a glenoid component according to the present invention.

FIG. 12 is a cross-section view taken along the plane designated 12—12 in FIG. 10 showing the bones of a shoulder joint and the glenoid component according to the present invention.

FIG. 13 is a cross-section view taken along the plane designated 13—13 in FIG. 10 showing the bones of a shoulder joint and the glenoid component according to the present invention.

FIG. 14 is a side section view of a alternative embodiment of a glenoid component according to the present invention.

DETAILED DESCRIPTION OF THE INVENTION

Referring to FIG. 1, the present invention is comprised generally of a cup 10 having three flanges 12, 14, 16.

Figure 2:
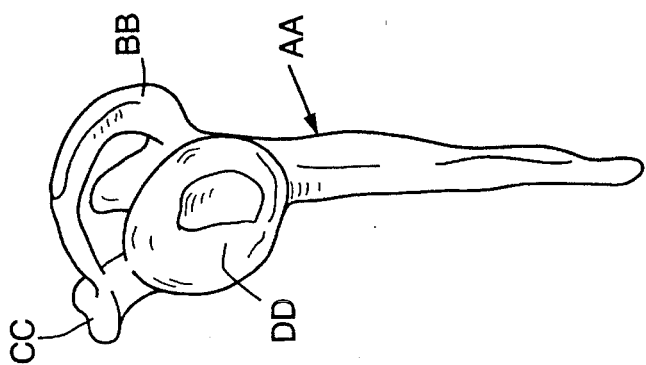
FIG. 2 is a lateral view of a scapula.
Figure 3:
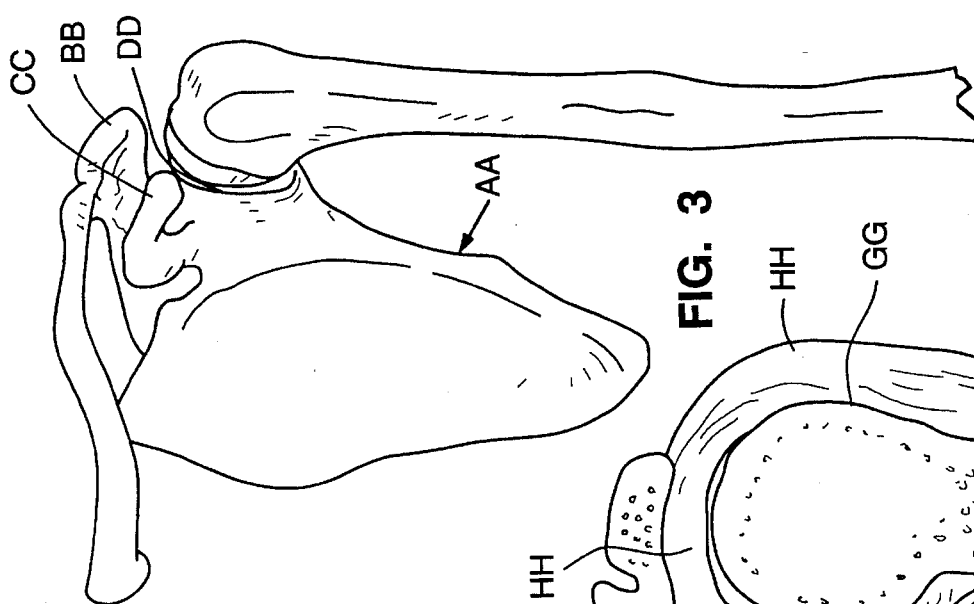
FIGS. 3 and 4 are an anterior and a posterior view, respectively, of the bones of a shoulder.
Figure 5:
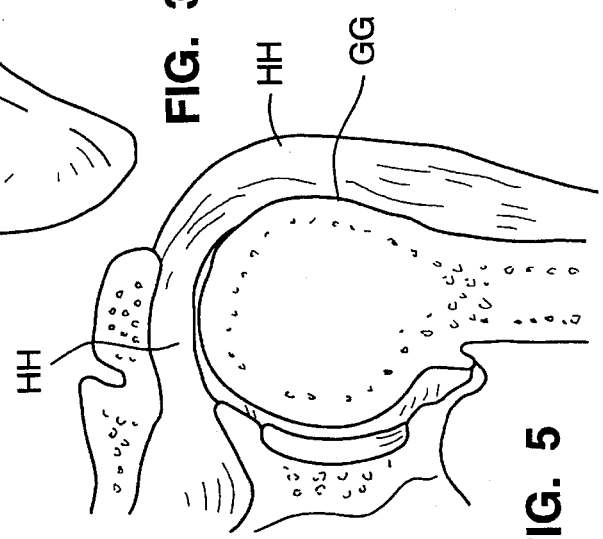
FIG. 5 is an cross-sectional anterior view of the shoulder joint showing the bones and soft tissue of the shoulder.
Figure 4:
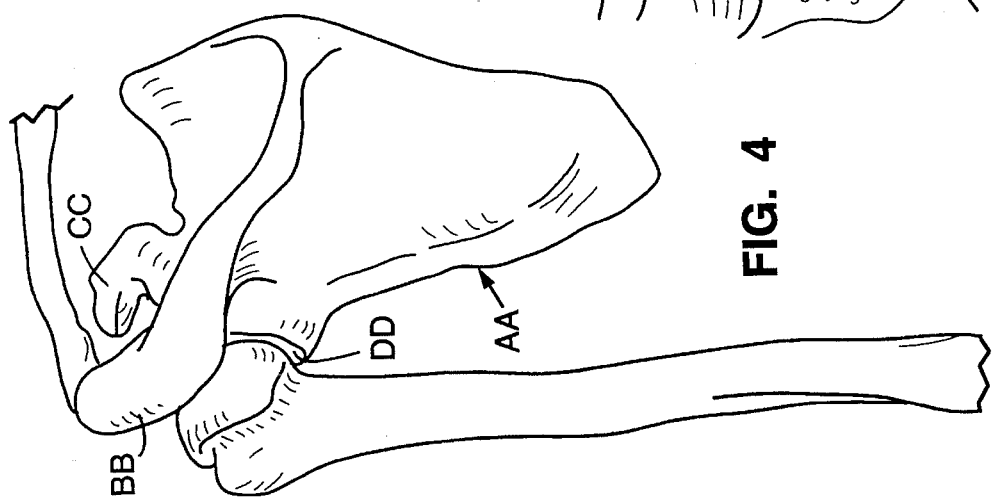

The configuration of the flanges will be best understood with reference to the anatomy of the shoulder, which is shown in FIGS. 2 through 5. FIG. 2 is a lateral view showing the scapula AA. The scapula AA includes the acromion BB, the coracoid process CC, and the glenoid fossa DD. When viewed from a lateral perspective, the acromion, coracoid process, and the lateral portion of the scapula AA come together to form a bone having an approximate "Y" shape. As shown in FIGS. 3 and 4, the glenoid fossa DD protrudes from the lateral side of the scapula and is slightly concave for articulation with the humeral head EE.

When an approximately semi-spherical hole is reamed into the glenoid fossa, a bony cup FF having the tri-flanged shape shown in FIG. 1 is exposed. The flanges 12, 14, 16 of the tri-flanged cup 10 are configured to approximate the tri-flanged configuration of the acromion, coracoid process, and scapula exposed by reaming, with flanges 12 and 14 corresponding to the coracoid process CC and acromion BB, respectively, and with flange 16 corresponding to a lip LL formed at the lateral portion of the scapula AA.

The tri-flanged cup 10 is constructed of an inner component 18 formed of biocompatible plastic material, such as polyethylene, and an outer component 20 of a biocompatible metal, such as a titanium metal alloy. The polyethylene component 18 is preferably approximately 4 mm in thickness. The cup 10, including the flanges 12, 14, 16, has an inward curvature, such that the outer surface of the cup 10 defines a sphere having a diameter of preferably 54–60 mm. The inner diameter of the cup 10 is preferably approximately 42–48 mm. These dimensions will vary depending on the size of the patient's shoulder and the amount of bone deterioration which has occurred in the patient's shoulder.

The edges of the polyethylene component 18 have a substantially flat portion 24 and a beveled portion 22. The beveled portion angles towards the interior of the cup. As will be described below, the angle of the beveled portion is selected to prevent the edges of the flanges 12, 14, 16 from obstructing motion of the humerus.

The metallic component 20 of the cup 10 preferably has an exterior surface which is capable of receiving bony ingrowth. The metallic component 20 has a plurality of bores 26. Screws 28 are provided for rigidly affixing the metallic layer 20 to the bone of the glenoid. Additional rigidity is provided as bone tissue begins to grow onto the porous exterior surface of the metallic component 20. A suitable adhesive (not shown) is provided for cementing the polyethylene component 18 to the metallic component 20 during implantation, after the metallic component is screwed into place.

The procedure for implanting the prosthesis of the present invention will next be described. Referring to FIG. 9, the glenoid fossa is reamed spherically about a reference center C to expose the tri-flanged bone configuration FF described above and shown in FIGS. 1 and 10. The metallic component 20 is next positioned against the tri-flanged bone configuration, using bone screws 28. Next, the polyethylene component 18 is cemented into place against the metallic component 20.

In order to optimize the range of motion of the shoulder, the reaming is preferably performed to a depth which will allow the tri-flanged cup 10 to be nested deeply within the reamed bony cup, i.e. such that only a small portion, if any, of the tri-flanged cut protrudes from the reamed bony cup FF. When the tri-flanged cup 10 is implanted in this manner, the bony cup FF cradles the tri-flanged cup and in doing so aids the control and stability of the joint. Moreover, because the bony cup and the tri-flanged cup 10 have similar contours at the flanges 12, 14, 16, the prosthesis does not add bulk to the shoulder which would otherwise be externally visible and thus cosmetically undesirable.

Finally, the patient's humerus is removed and a prosthetic humeral component 29 having a head 30 and a porous coated stem 32 (see FIG. 1) is implanted using conventional techniques. The head 30 of the prosthetic humerus is positioned within the cup 10 to allow it to articulate against the plastic component 18 during movement of the arm. Over time, bone grows into the metallic exterior surface 20 of the tri-flanged cup 10 and thereby increases the integrity of the attachment between the glenoid component and the reamed glenoid. Bone likewise grows into the stem 32 of the humeral component 29.

Dotted line XX has been drawn in FIG. 13 to illustrate the benefits of the beveled edges 22 of the tri-flanged cup 10. But for the beveled edges 22, the ends of the flanges 12, 14, 16 would extend out to line XX. As can be seen, this would reduce the amount by which the humeral component 29 could rotate within the tri-flanged cup 10 before colliding with the ends of the flanges 12, 14, 16. The angle of the beveled edges 22 is thus chosen to optimize the degree of movement by optimizing the angle through which the humeral component 29 can be rotated without obstruction by the tri-flanged cup 10.

The tri-flanged cup 10 provides a surface (specifically, the plastic component 18) upon which the prosthetic humeral head can articulate. Because the cup is broader than conventional ball and socket joints, it allows enhanced range of motion over those cups. The depth of the cup and the inward curvature of the flanges prevents migration of the humeral head, while the breadth of the cup maximizes the patient's range of movement. Moreover, because the flanges are contoured to align with the tri-flanged configuration of bone created by reaming, the cup normally cannot be noticed through the skin and does not cause the shoulder to appear deformed.

FIG. 14 shows an alternative embodiment 10a of a tri-flanged cup according to the present invention. In this embodiment, the center of curvature C1 of the metallic exterior component 20a is offset from the center of curvature C2 of the plastic interior component 18a.

A tri-flanged cup of this type is useful for patients having substantial bone deterioration in the glenoid region. In some patients having such deterioration, the first embodiment of the tri-flanged cup may sit slightly askew against the glenoid following implantation (unless cement or other filler material is used to fill the gap caused by the deteriorated bone) since a portion of the tri-flanged cup will sit within a cavity caused by the deterioration.

The off-set centers of the alternative embodiment of the tri-flanged cup 10a result in a cup having a thicker portion 34 which is designed to be positioned in a region of severe bone degradation. This allows the tri-flanged cup to be oriented to properly receive the humeral component and thus provides an axis of rotation of the humerus that is more closely related to a normal one.

Naturally, the specific amount by which the centers are offset (and whether the offset occurs near the top or bottom of the cup) depends upon the degree and location of the degradation in a particular patient.

Conclusion

The tri-flanged cup according to the present invention has been described with respect to two exemplary embodiments. However, it should be understood that the described embodiments are not intended in a limiting sense. The scope of the present invention is intended to be limited only in terms of the appended claims.

What is claimed is:

1. A prosthetic glenoid for implantation in a bony cup formed by reaming a human glenoid and for providing an articulating surface for a humeral head, the prosthetic glenoid comprising:

(a) a tri-flanged cup proportioned to fit within a bony cup formed in a glenoid in a patient's shoulder by reaming the glenoid to a depth at which an approximate Y-shaped configuration of an acromion, a coracoid process, and a scapula is exposed, the tri-flanged cup comprised of first, second and third flanges and each of said flanges terminating at a free end such that said tri-flanged cup is configured for at least partially containing a humeral head within the tri-flanged cup; and (b) securing means for securing the cup within the bony cup such that the first, second, and third flanges are spaced to approximately align with and adjacent to the acromion, the coracoid process, and the scapula, respectively.

2. The prosthetic glenoid of claim 1 wherein the tri-flanged cup has an interior surface defined by a first center of curvature and an exterior surface defined by a second center of curvature which is offset from the first center of curvature.

3. A method of repairing a shoulder joint, the method comprising the steps of:

(a) reaming a glenoid to produce a cup-shaped region having an approximately Y-shaped configuration of an acromion, a coracoid process, and a scapula;

(b) providing a tri-flanged cup having first, second and third flanges and each of said flanges terminating at a free end, said tri-flanged cup having a substantially smooth interior surface, and further providing a humeral head;

(c) positioning the tri-flanged cup such that the first, second, and third flanges are approximately aligned with and adjacent to the acromion, coracoid process, and scapula, respectively; and (d) positioning the humeral head to articulate within the cup-shaped region.

4. The method of claim 3 wherein step (b) includes providing a tri-flanged cup having an interior surface defined by a first center of curvature and an exterior surface defined by a second center of curvature which is offset from the first center of curvature.

* * * * *